(12) United States Patent
Linares

(10) Patent No.: US 12,011,360 B2
(45) Date of Patent: Jun. 18, 2024

(54) EXPANDABLE SPINAL JACK FOR INSTALLATION BETWEEN UPPER AND LOWER SUCCEEDING SUPERIOR ARTICULAR PROCESSES

(71) Applicant: Linares Spinal Devices, LLC, Auburn Hills, MI (US)

(72) Inventor: Miguel A. Linares, Bloomfield Hills, MI (US)

(73) Assignee: Linares Spinal Devices, LLC, Aurburn Hills, MI (US)

( * ) Notice: Subject to any disclaimer, the term of this patent is extended or adjusted under 35 U.S.C. 154(b) by 0 days.

(21) Appl. No.: 17/967,968

(22) Filed: Oct. 18, 2022

(65) Prior Publication Data

US 2023/0130877 A1 Apr. 27, 2023

Related U.S. Application Data

(60) Provisional application No. 63/270,784, filed on Oct. 22, 2021.

(51) Int. Cl.
*A61F 2/44* (2006.01)
*A61F 2/30* (2006.01)

(52) U.S. Cl.
CPC .. *A61F 2/4405* (2013.01); *A61F 2002/30166* (2013.01); *A61F 2002/30505* (2013.01); *A61F 2002/30525* (2013.01); *A61F 2002/3055* (2013.01); *A61F 2002/30892* (2013.01)

(58) Field of Classification Search
CPC ............ A61B 17/7062; A61B 17/7065; A61B 17/7067; A61B 17/7068
See application file for complete search history.

(56) References Cited

U.S. PATENT DOCUMENTS

| | | | |
|---|---|---|---|
| 8,048,118 B2 * | 11/2011 | Lim | A61B 17/7062 606/248 |
| 8,574,267 B2 * | 11/2013 | Linares | A61F 2/442 606/248 |
| 8,585,738 B2 | 11/2013 | Linares | |
| 8,613,758 B2 | 12/2013 | Linares | |
| 8,617,212 B2 | 12/2013 | Linares | |
| 8,623,056 B2 | 1/2014 | Linares | |
| 8,728,123 B2 | 5/2014 | Bucci et al. | |
| 9,247,968 B2 | 2/2016 | Taber et al. | |
| 9,326,797 B2 | 5/2016 | Pinville et al. | |
| 9,474,626 B2 * | 10/2016 | Jimenez | A61F 2/447 |
| 9,480,502 B2 * | 11/2016 | Whiton | A61B 17/7068 |
| 9,561,060 B2 | 2/2017 | Taber et al. | |
| 9,775,718 B2 | 10/2017 | Taber et al. | |
| 9,913,667 B2 | 3/2018 | Dinville et al. | |
| 9,968,381 B2 | 5/2018 | Thalgott et al. | |
| 10,076,422 B2 | 9/2018 | Zappacosta et al. | |

(Continued)

*Primary Examiner* — Ellen C Hammond
*Assistant Examiner* — Holly Joanna Lane
(74) *Attorney, Agent, or Firm* — Dinsmore & Shohl LLP

(57) ABSTRACT

A spinal jack adapted for installation between first and second vertebral processes, including a central body supporting first and second inter-expandable jack halves between retracted and expanded positions. Each of the jack halves further includes gripping portions adapted for engaging the vertebral processes. A geared mechanism provides for expanding or retracting the jack halves in order to establish a corrected adjusted orientation between the processes.

5 Claims, 19 Drawing Sheets

(56) References Cited

U.S. PATENT DOCUMENTS

| | | |
|---|---|---|
| 10,398,478 B2 | 9/2019 | Ganter et al. |
| 10,478,232 B2 | 11/2019 | Pool et al. |
| 10,517,652 B2 | 12/2019 | Dinville et al. |
| 10,543,024 B2 | 1/2020 | Lee et al. |
| 10,695,189 B2 | 6/2020 | Li et al. |
| 10,751,094 B2 | 8/2020 | Green et al. |
| 10,792,078 B2 | 10/2020 | Smisson, III et al. |
| 10,835,297 B2 | 11/2020 | Altarac et al. |
| 11,065,040 B2 | 7/2021 | Zappacosta et al. |
| 2007/0100340 A1* | 5/2007 | Lange ............... A61B 17/7065 606/279 |
| 2007/0233098 A1* | 10/2007 | Mastrorio .......... A61B 17/7065 606/86 A |
| 2009/0209965 A1 | 8/2009 | Lewis |
| 2010/0106190 A1* | 4/2010 | Linares ............. A61B 17/7067 606/249 |
| 2011/0184468 A1 | 7/2011 | Metcalf, Jr. et al. |
| 2011/0313467 A1 | 12/2011 | Youssef et al. |
| 2012/0004727 A1 | 1/2012 | Ben-Mokhtar et al. |
| 2012/0109205 A1 | 5/2012 | Mitchell et al. |
| 2012/0226314 A1 | 9/2012 | Chin et al. |
| 2012/0253393 A1 | 10/2012 | Fiorella |
| 2013/0103087 A1 | 4/2013 | Grizzard |
| 2013/0184754 A1 | 7/2013 | Taber et al. |
| 2013/0197581 A1 | 8/2013 | Justis et al. |
| 2013/0296939 A1* | 11/2013 | Perkins ............. A61B 17/7068 606/279 |
| 2015/0164656 A1 | 6/2015 | Zappacosta et al. |
| 2015/0313650 A1 | 11/2015 | Taber et al. |
| 2015/0359640 A1 | 12/2015 | Taber et al. |
| 2016/0007983 A1 | 1/2016 | Frey et al. |
| 2016/0022324 A1 | 1/2016 | Yoon et al. |
| 2017/0319351 A1 | 11/2017 | Bechtel et al. |
| 2017/0333091 A1 | 11/2017 | Taber et al. |
| 2018/0078381 A1 | 3/2018 | Taber et al. |
| 2018/0263667 A1 | 9/2018 | Dinville et al. |
| 2019/0159812 A1 | 5/2019 | Zappacosta et al. |
| 2019/0201057 A1 | 7/2019 | Altarac et al. |
| 2020/0038071 A1 | 2/2020 | Pool et al. |
| 2020/0297392 A1 | 9/2020 | Zappacosta et al. |
| 2021/0052307 A1 | 2/2021 | Soo et al. |
| 2021/0169657 A1 | 6/2021 | Bechtel et al. |
| 2021/0204985 A1 | 7/2021 | Choi et al. |

* cited by examiner

EXPANDABLE SPINAL JACK FOR INSTALLATION BETWEEN UPPER AND LOWER SUCCEEDING SUPERIOR ARTICULAR PROCESSES

CROSS REFERENCE TO RELATED APPLICATIONS

The present application claims the priority of U.S. Ser. No. 63/270,784 filed Oct. 22, 2021.

FIELD OF THE INVENTION

The present invention relates generally to spinal jacks for providing inter-vertebral support. More specifically, the present invention teaches an adjustable spinal jack for installation between superior articular processes of upper and lower succeeding vertebrae.

BACKGROUND OF THE INVENTION

Spinal jacks designs are known in the prior art for providing adjusted and secure positioning support between succeeding spinal vertebra. Examples of these are depicted in each of Linares U.S. Pat. No. 8,623,056 and Linares U.S. Pat. No. 8,585,738.

SUMMARY OF THE PRESENT INVENTION

The present invention discloses an in-situ adjustable spinal jack which is adapted for installation between first and second vertebral processes. The jack includes a central body supporting first and second inter-expandable jack halves between each of retracted and expanded positions.

Each of the jack halves further includes gripping portions adapted for engaging the successive vertebral processes associated with a patient's spine. The gripping portions further include a pair of spaced apart arms defining a pocket adapted to receive the vertebral process therebetweeen. The pockets each further include textured surfaces for providing additional gripping of the vertebral processes.

A geared mechanism provides for expanding or retracting the jack halves in order to establish a corrected adjusted orientation between the selected processes. The geared mechanism further can have a tool bit engageable drive gear and inter-engaging outer driven gears which in turn displace the jack halves relative to the central body. A tool bit engageable worm gear extends through the main body, with a linkage mechanism extending from portions supported upon the worm gear to the jack halves and, in response to rotary actuation of the gear, in turn displaces the jack halves relative to the body. The linkage further includes at least one pair of scissor lifts extending between said jack halves.

A spring provides an outward bias against the jack halves. The body and inter-expandable jack halves can further include any medical grade metal or plastic. The drive gear further includes a spring-loaded pin for preventing displacement of the jack halves without engagement of the tool bit. A plurality of circumferential extending and coaxial skirt portions, upon expanding the jack halves, are also provided for isolating an interior of the body.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

With reference to the attached illustrations, the present invention discloses a number of variants of an adjustable spinal jack for installation between superior articular processes of upper and lower succeeding vertebrae. A general representation of a selected jack associated with a first variant in FIGS. 2-7 is initially depicted environmentally at 10 in FIG. 1 and is shown positioned between upper 2 and lower 4 successive superior articular processes corresponding to upper 6 and lower 8 vertebrae.

As will be described in further detail with reference to the succeeding embodiments, the present invention provides an expandable spinal jack which overcomes many of the disadvantages of the prior art and provides an effective solution for stabilizing and fixing in position a given orientation established between the succeeding vertebrae. As will be further described, the spinal jack designs described herein further permit in situ adjustment, at any future time following initial surgical implantation, in a minimally invasive fashion and in order to re-adjust the spatial positioning established between the upper and lower halves of each variant of the spinal jack, such as in order to compensate and correct for downstream vertebral complications following the initial implantation of the spinal jack.

Figure 1:
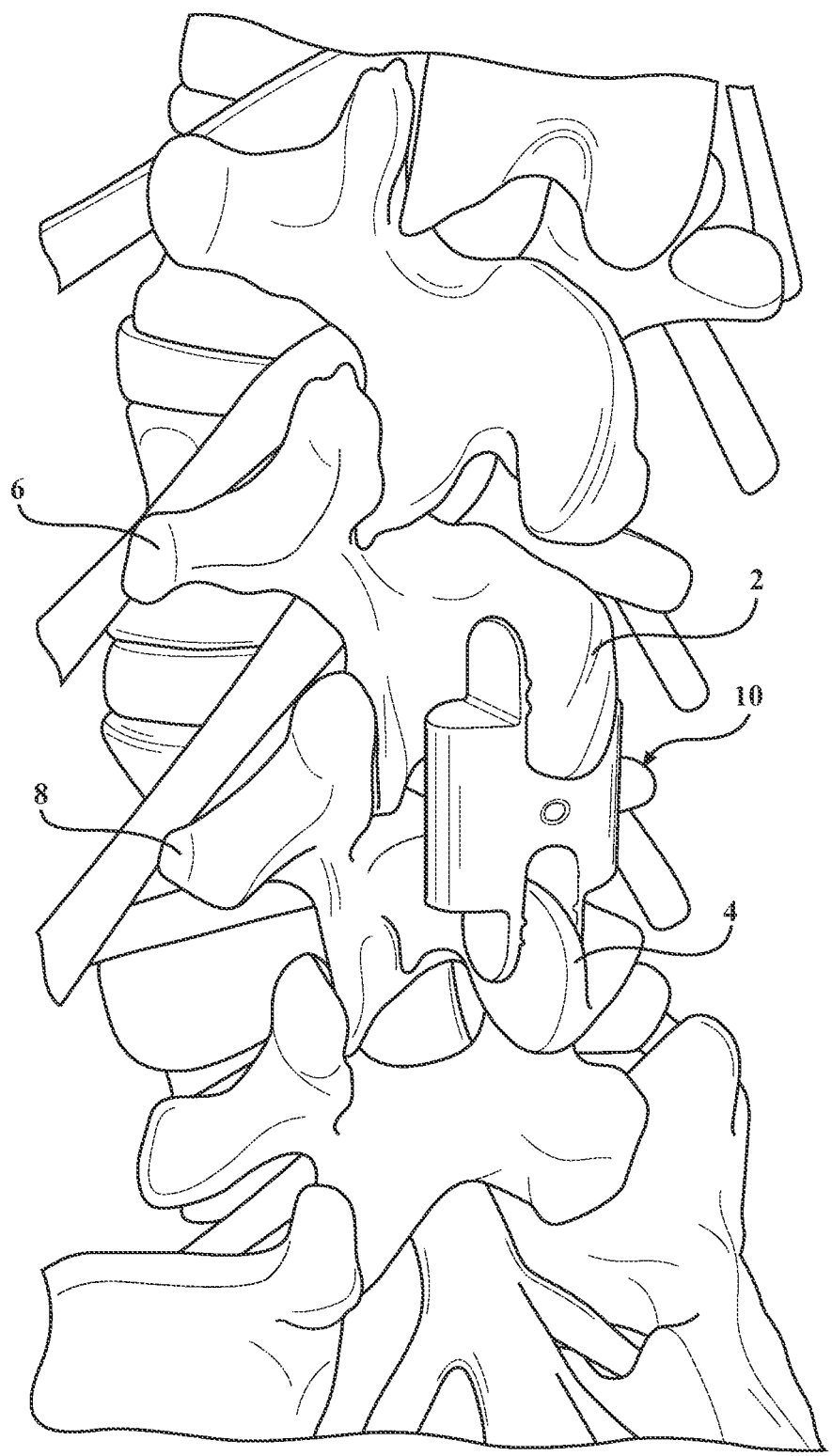
FIG. 1 is an environmental illustration of a spinal jack according to one non-limiting variant installed between succeeding superior articular processes associated with upper and lower consecutive spinal vertebra.
Figure 2:
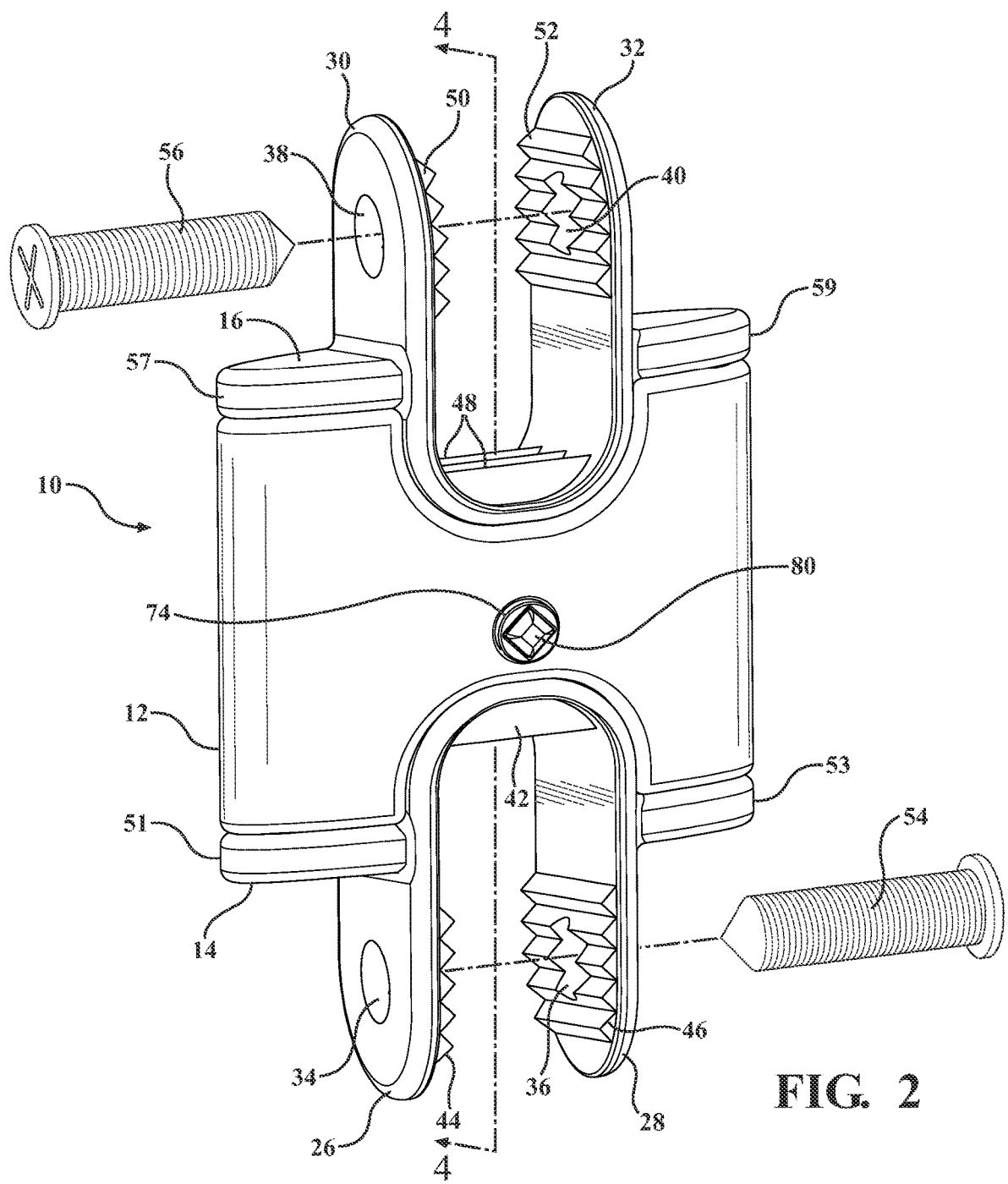
FIG. 2 is a perspective view of a spinal jack substantially as shown in FIG. 1 in a retracted position.

Proceeding to FIG. 1, an environmental illustration is generally shown of the spinal jack 10 substantially as shown in FIG. 1 in a retracted position. In combination with the closed position of FIG. 2 and expanded position FIG. 3, the spinal jack includes a three dimensional and arcuate ergonomic central body 12 supporting each of a lower expandable half 14 and an upper expandable half 16. The central body 12 and outer (lower/upper) bodies 14/16 are each constructed of a suitable sanitary medical grade material not limited to a metal or plastic composition.

Figure 3:
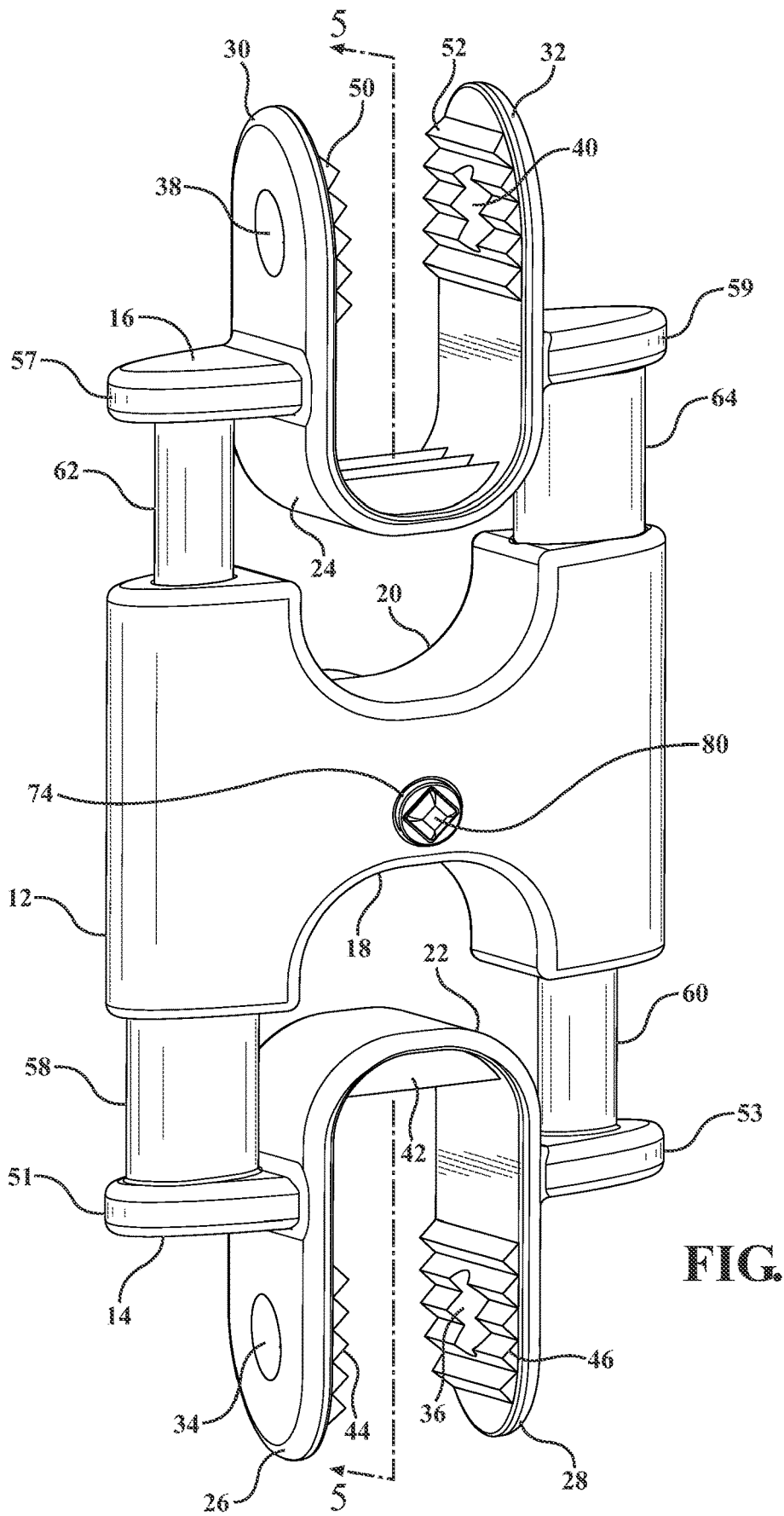
FIG. 3 is a succeeding view of the spinal jack of FIG. 2 in an expanded position.
Figure 5:
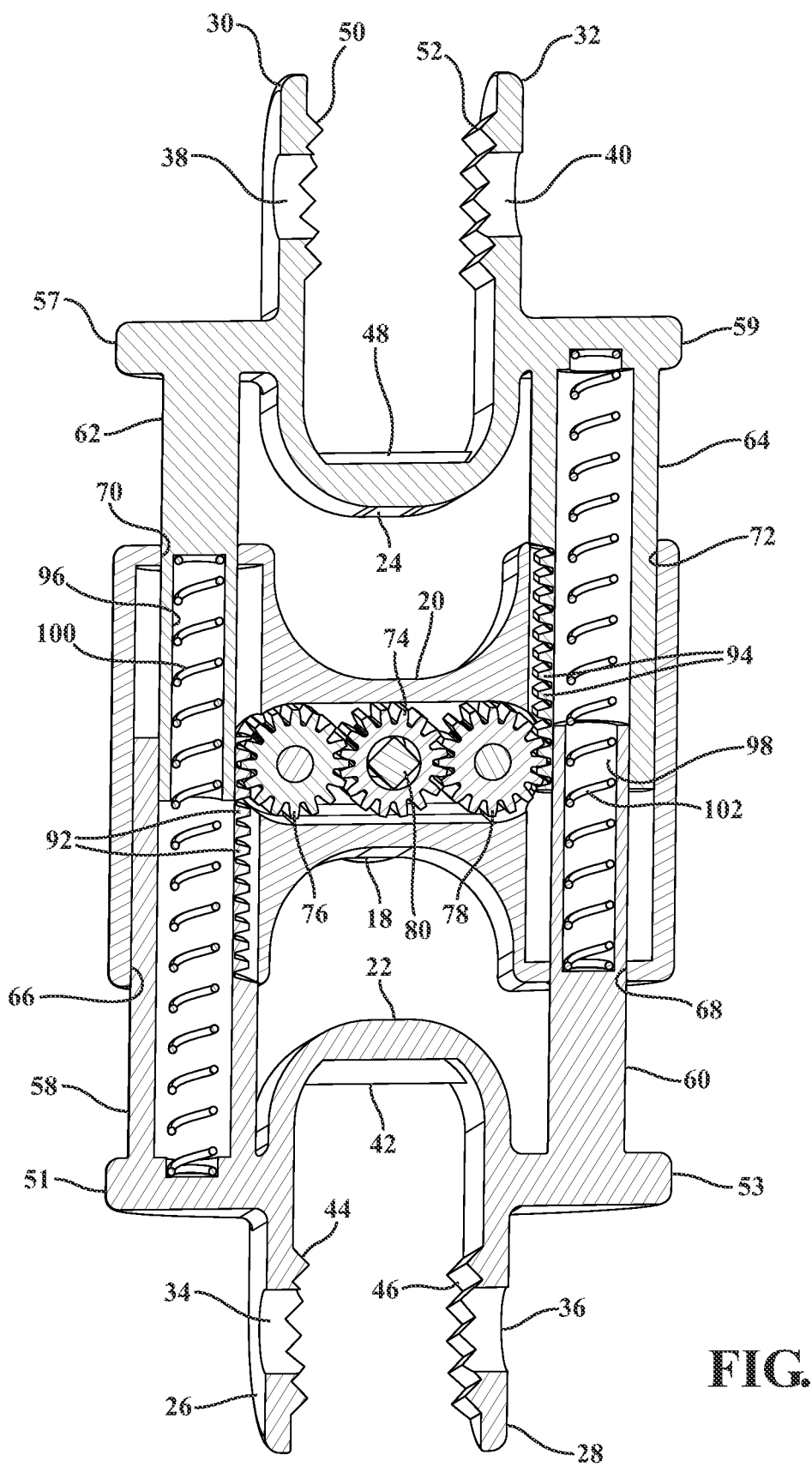
FIG. 5 is a length cutaway taken along line 5-5 of FIG. 3 and depicting the interior gearing and spring biased configuration of the spinal jack in the expanded position for separating the upper and lower halves.
Figure 6:
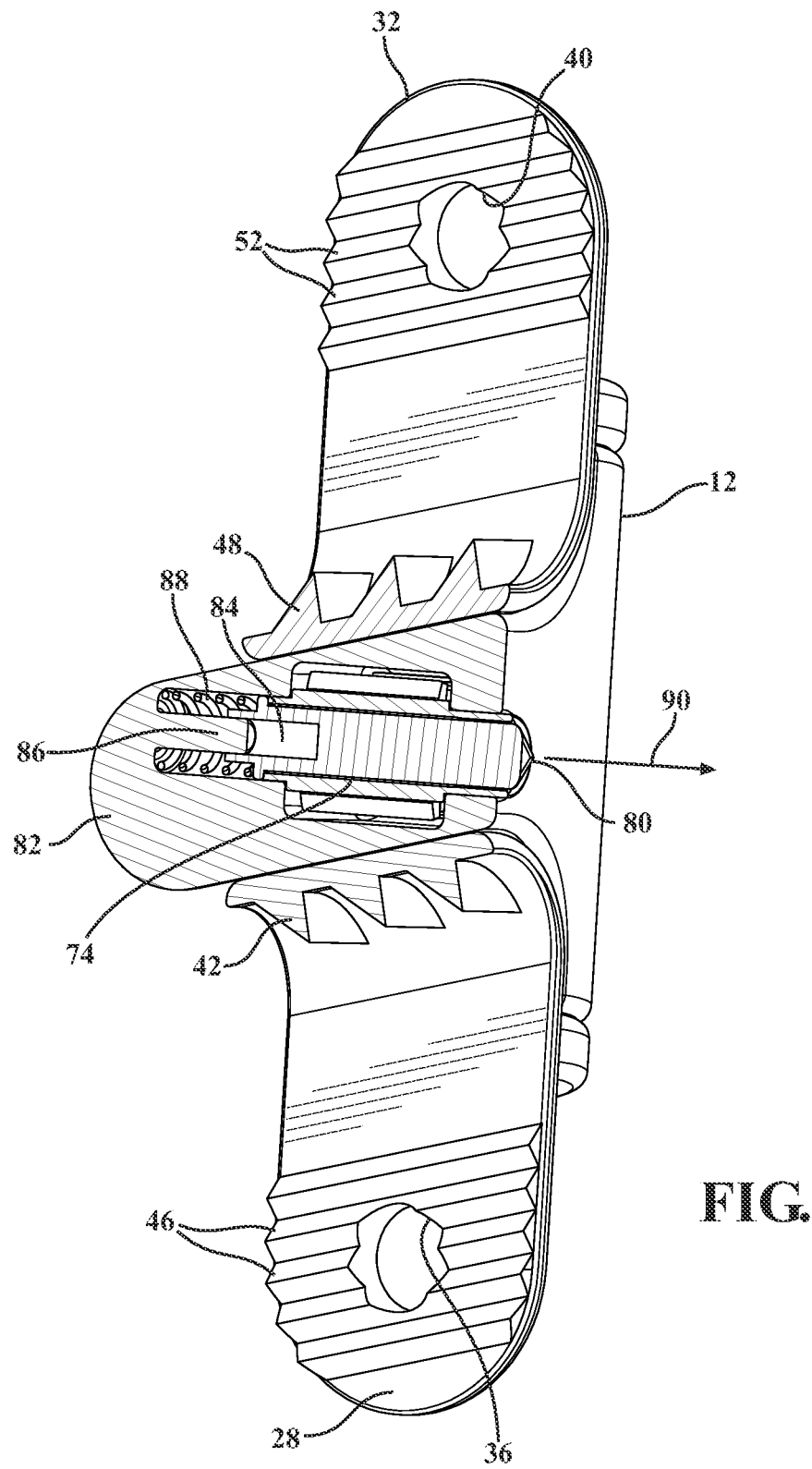
FIG. 6 is a further cutaway taken along line 6-6 of FIG. 4 and depicting the features of the spring loaded lock pin associated with the central adjustment gear for preventing relative movement of the spinal jack halves once released.
Figure 7:
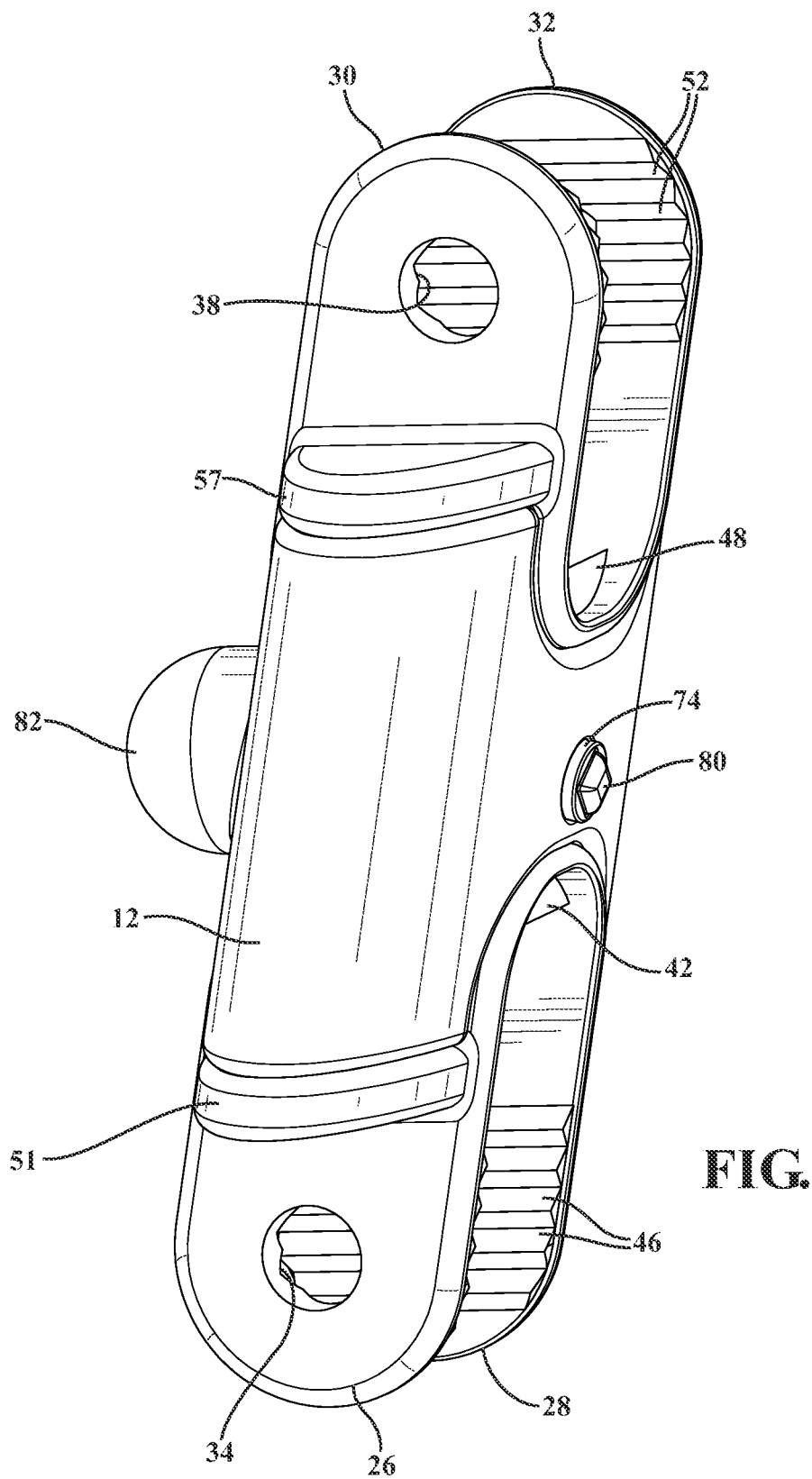
FIG. 7 is a rotated perspective of the spinal jack of FIG. 2 viewed from another angle.

The central body 12 in profile depicts a substantial "H" shape with inwardly contoured or recessed bottom 18 and top 20 facing surfaces (see as best shown in FIG. 3) for seating central gripping portions (further as best shown in FIGS. 3 and 5 at 22 and 24) associated with each of the lower 14 and upper 16 inter-expandable jack halves. Each of the gripping portions 22 and 24 further exhibits a substantially "U" shape with aligning apertures configured in spaced apart and extending legs (see pairs 26/28 and 30/32 for each gripping portion 22 and 24, respectively). The aligning apertures are further defined by spaced apart pairs of inner perimeter extending edges (at 34/36 for lower gripping portion 22 and further at 38/40 for upper gripping portion 24).

With reference again to FIG. 1, the spaced apart pairs of legs 26/28 and 30/32 of the opposite extending gripping portions 22 and 24 are adapted to seat the upper 2 and lower 4 consecutive superior articular processes, The inner "U" shaped surface profile of each of the gripping portions is further exhibited by any type of textured or ribbed profile (see at inner base surface 42 and inner side surfaces 44/46 for the lower gripping portion 22 as well as inner base surface 48 and inner side surfaces 50/52 for the upper gripping portion 24) the purpose of which is to provide additional resistive engagement against the facet surfaces of the processes 2 and 4.

Also shown are screw type fasteners 54 and 56 (see FIG. 2) which, upon positioning and the gripping portions and drilling through the processes 2 and 4, anchor the lower 14 and upper 16 jack halves to the respective vertebrae. Alternatively, the gripping portions can be crimped into engagement with the vertebral processes 2 and 4 without the use of separate screws.

Each of the lower 14 and upper 16 spinal jack halves (or portions) provide respective outer and inner integrally formed and parallel spaced telescoping portions, these being supported by outer lateral ledge or shoulder locations of each of the spinal jack halves (see at 51/53 for lower jack half 14 and at 57/59 for upper jack half 16) and are shown by elongated telescoping portions (outer 58 and inner 60) for the lower spinal jack 14 along with upper jack 16 elongated telescoping portions, which are shown at 62 and 64. As further best depicted in FIGS. 4-5, selected telescoping portions 60 and 62 define inner telescoping portions which are received inside each of the opposing outer portion 58 of the lower jack half 14 (by inner telescoping portion 62) and outer telescoping portion 64 opposing the inner telescoping portion 60 of the lower jack 14.

Figure 4:
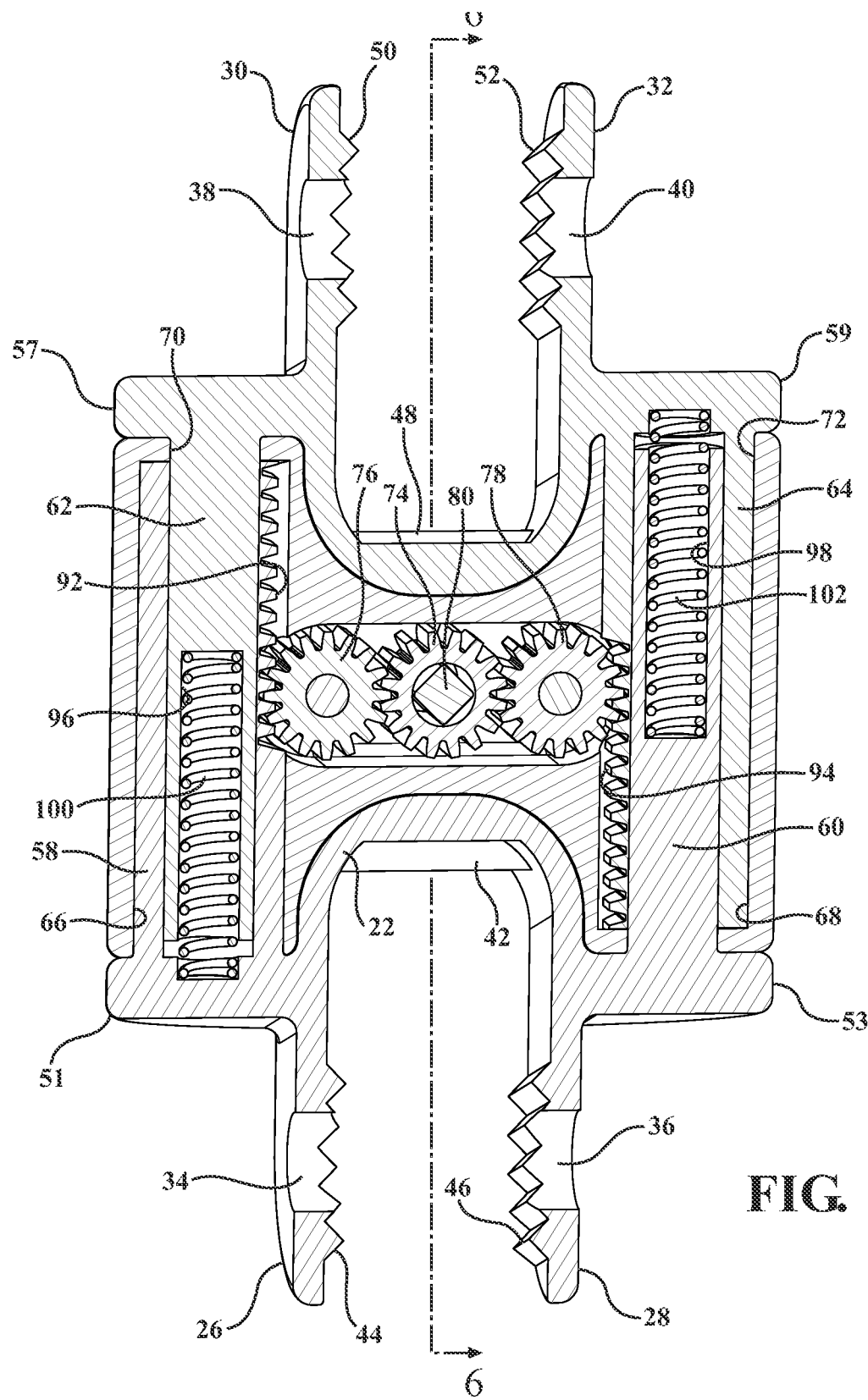
FIG. 4 is a length cutaway taken along line 4-4 of FIG. 2 and depicting the interior gearing and spring biased configuration of the spinal jack in the retracted position.

The central body 12 includes upper and lower pairs of rim defining apertures for receiving the telescoping lower 58/60 and upper 62/64 pairs of opposing and inter-telescoping jack portions, these shown in FIGS. 4 and 5 by lower receiving inner perimeter rim apertures 66/68 and upper receiving inner perimeter rim apertures 70/72, such that the central body 12 defines a pair of elongated passageways extending its height for receiving the opposing telescoping portions 58/60 and 62/64 of the lower 14 and upper 16 spinal jack halves.

The length cutaway views of FIGS. 4-5 best illustrate gearing for expanding and retracting the jack halves relative to one another. These include a central gear 74 and a pair of inter-engaging outer gears 76 and 78 arranged on opposite sides of the central gear 74. As further shown in the further cutaway view of FIG. 6, a spring loaded and hex shaped lock pin 80 is provided associated with the central adjustment gear for preventing relative movement of the spinal jack halves 14/16 once released.

The spring loaded pin 80 is seated within a central enlargement 82 (see FIGS. 6-7) of the central body 12 such that a recessed interior passageway 84 (FIG. 6) formed in an inner end of the spring pin 80 aligns with an opposing inner stem 86 defined within an interior passageway of the central body 12. A displacement coil spring 88 biases the spring loaded pin 80 outwardly in the direction of arrow 90 shown in FIG. 6 until, and upon a tool bit (not shown) being inserted in a counter direction against the bit head configuration of the gear 74, the pin 80 is displaced in an opposite inward direction to a point at which the forward portion of the pin 80 clears an opposing inner hex surface profile of the inner aperture defined in the central drive gear 74. At this point, the inserting tool permits rotation of the central gear 74 and corresponding outer gears 76/78.

Referring again to the interior cutaway views of FIGS. 4-5, linear gear tooth profiles are configured at each of 92 along the lower/outer telescoping portion 58 (engaged by teeth of first outer gear 76), as well as at 94 along the upper/outer telescoping portion 72 (engaged by teeth of second outer gear 78). Each of the upper/inner telescoping portion 62 and lower/inner telescoping portion 60 further include an inner passageway or pocket (see at 96 and 98) which respectively receive additional coil springs 100 and 102, these extending from the pockets 96/98 into adjoining and defined interiors of the telescoping portions (58 lower and 64 upper), with the ends of the spring 100 and 102 biasing inner opposite end walls of the collectively defined interior passageways for influencing the lower 14 and upper 16 jack halves in opposite/outward expanding directions.

In this fashion, rotation of the central drive gear 74 in the clockwise direction from the vantage of the retracted configuration of FIG. 4, causes the opposing counter rotation of the outer gears 76/78, resulting in the upper 16 and lower 14 jack halves being simultaneously and outwardly separated/expanded in the manner depicted in the cutaway of FIG. 5, and as further assisted by the outward expanding bias exerted by the enclosed springs 100/102. In a typical installation protocol, the spinal jack 10 is initially surgically implanted in the manner depicted in FIG. 1, with the gripping portions of the opposing spinal jack halves being initially affixed/anchored to the successive superior articular processes 2/4.

Subsequent expanding adjustment results from insertion of the suitable tool bit (not shown) in biasing fashion against the hex configured pin 80 in order to inwardly displace the same and to unlock the central drive gear 74 (see again FIG. 6), in turn enabling rotation of the same for incrementally expanding the spinal jack halves in order to adjust a desired spatial positioning established between the processes 2 and 4 as desired, such as in order to alleviate patient pain/discomfort resulting for vertebral misalignments. As further understood, additional spinal braces and the like can be provided (not shown) which can be installed against the later processes of each vertebrae (see by example shown at 6 and 8 in FIG. 1) and in order to provide additional vertebral support depending upon the nature of the spinal injury being addressed.

Figure 8:
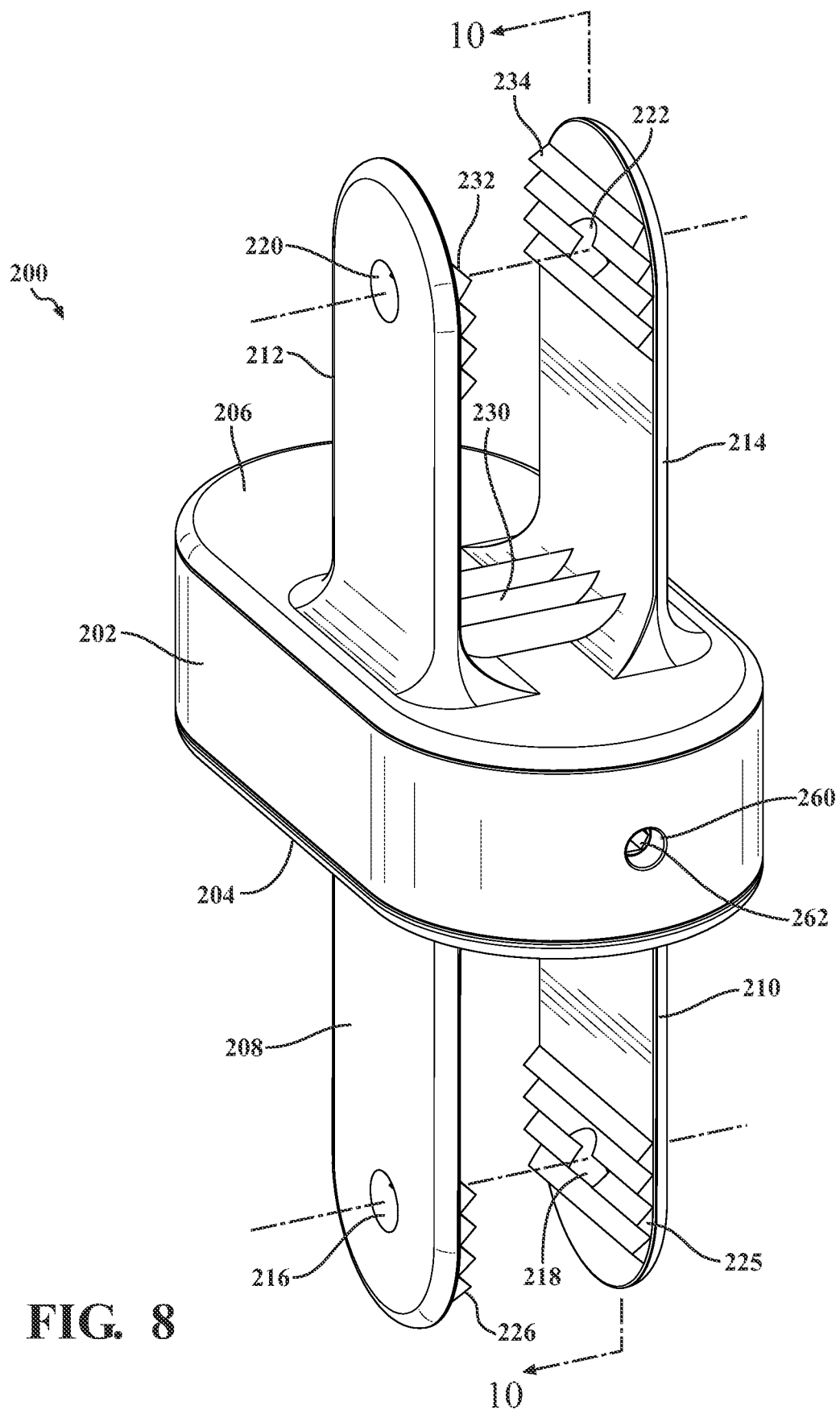
FIG. 8 is a perspective view of a combination worm screw and axial displacement linkage spinal jack assembly in a retracted position and according to a further variant.

Proceeding to FIG. 8, a perspective view of a combination worm screw and axial displacement linkage spinal jack assembly is generally shown at 200 in a retracted position and according to a further variant. A number of the structural features of the spinal jack 200 are repeated from the original variant 10 and include a reconfigured central body 202 with lower 204 and upper 206 displaceable spinal jack halves.

The central body 202 and outer (lower/upper) bodies 204/206 are each again constructed of a suitable sanitary plastic or metal. The central body 202 in profile depicts a generally oval shape for seating the spinal jack bodies 204/206 in the retracted position of FIG. 8.

Each of the jack halves 204/206 incorporates a pair of spinal process gripping legs similar to that previously described, and as shown at 208/210 for lower body 204 and further at 212/214 for upper body 206). Aligning apertures are further defined through the lower and upper pairs of legs as shown at 216/218 and 220/222.

Similar to the first embodiment, the spaced apart pairs of legs 208/210 and 212/214 of the opposite extending gripping portions are adapted to seat the upper 2 and lower 4 consecutive superior articular processes (see again FIG. 1), The pairs of legs again define a substantially inner "U" shaped surface profile of each of the gripping portions is further exhibited by any type of textured or ribbed profile (see at inner base surface 224 in FIGS. 10-11, along with inner side surfaces 226/228 for the lower gripping portion as well as inner base surface 230 and inner side surfaces 232/234 for the upper gripping portion) the purpose of which is again to provide additional resistive engagement against the facet surfaces of the processes 2 and 4. Also previously shown in FIG. 2, screw type fasteners, again at 54 and 56 are provided and which, upon positioning and the gripping portions and drilling through the processes 2 and 4, anchor the lower 204 and upper 206 jack halves to the respective vertebrae.

Figure 9:
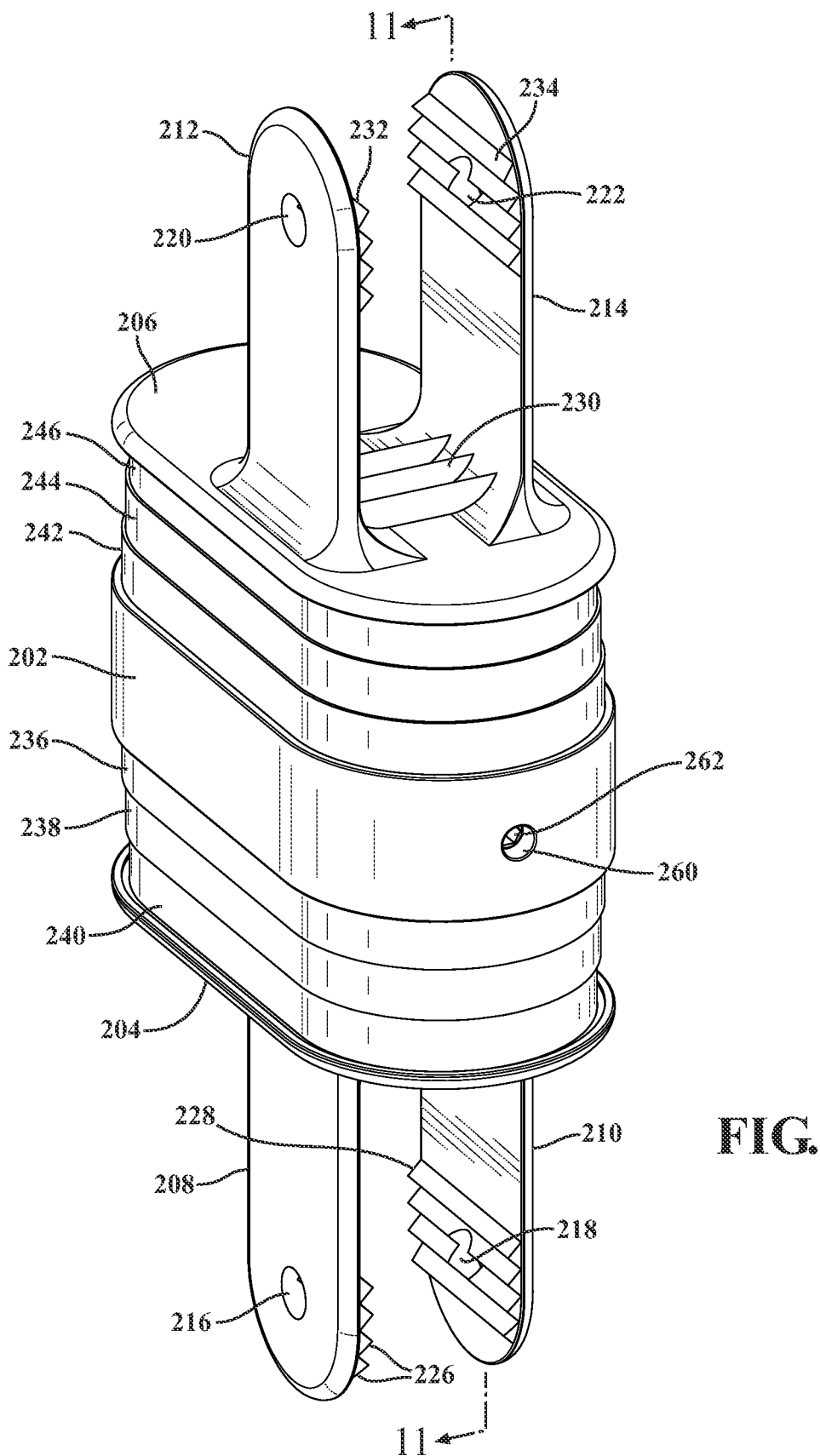
FIG. 9 a succeeding view to FIG. 8 depicting the spinal jack in an expanded position.

FIG. 9 a succeeding view to FIG. 8 depicting the spinal jack in an expanded position and which includes pluralities of lower and upper telescoping and overlapping skirt portions (see as shown in descending cross sectional dimensions for each of lower 236, 238 and 240 and upper 242, 244 and 246 skirts which can either nest or expand as shown). As best shown in the retracted and expanded cutaway views of FIGS. 10-11, the individual skirts nest within circumferential extending pockets (best shown at 248 and 250 in FIG. 11) defined around lower and upper perimeter extending locations in the central body 202 so that, and upon expanding, the skirts isolate and protect the interior of the body separating the base surfaces of the lower and upper jack halves (again at 204/206).

Figure 10:
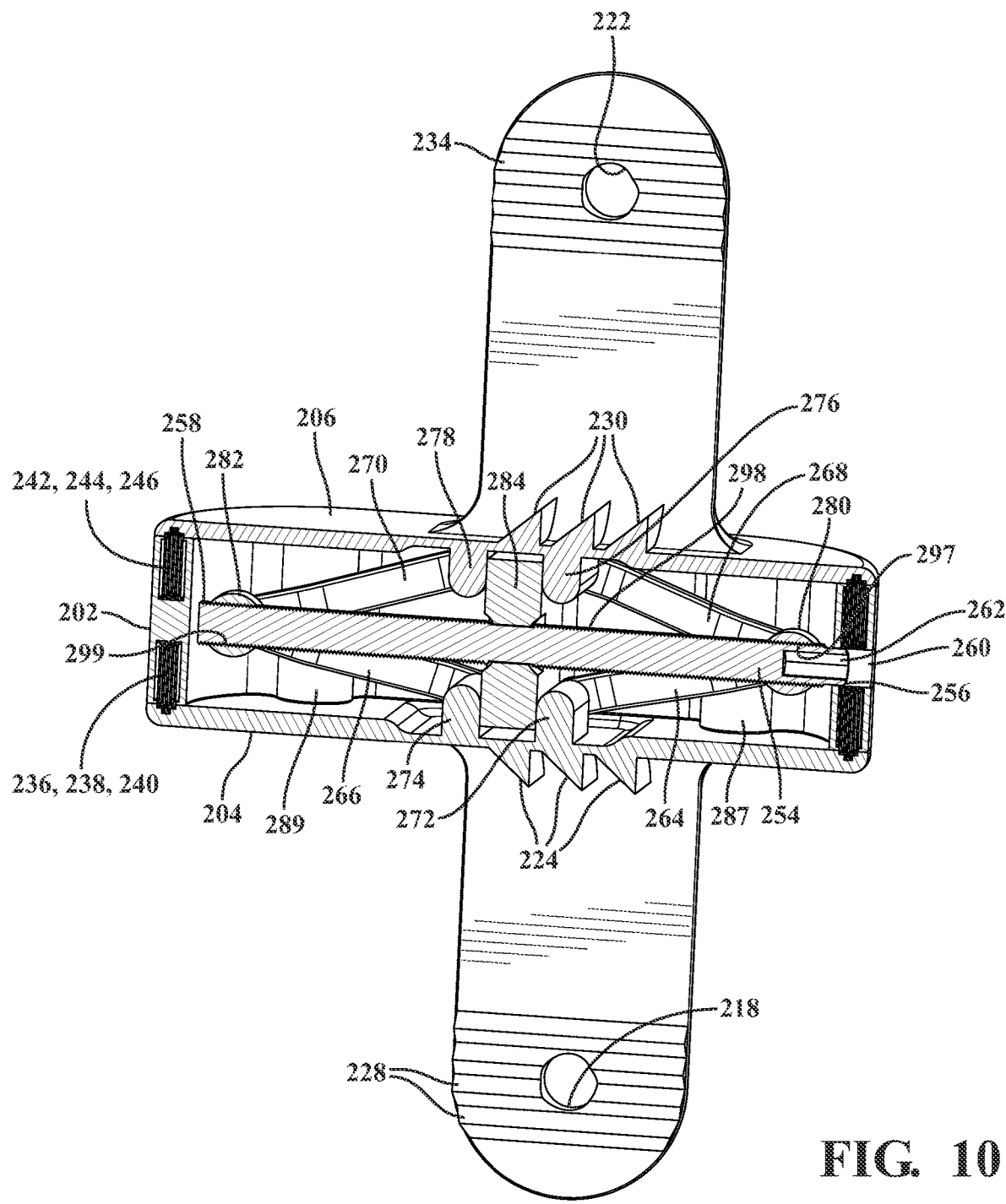
FIG. 10 is a length cutaway view taken along line 10-10 of FIG. 8 and depicting the worm screw and axially translating linkages in the retracted position.
Figure 11:
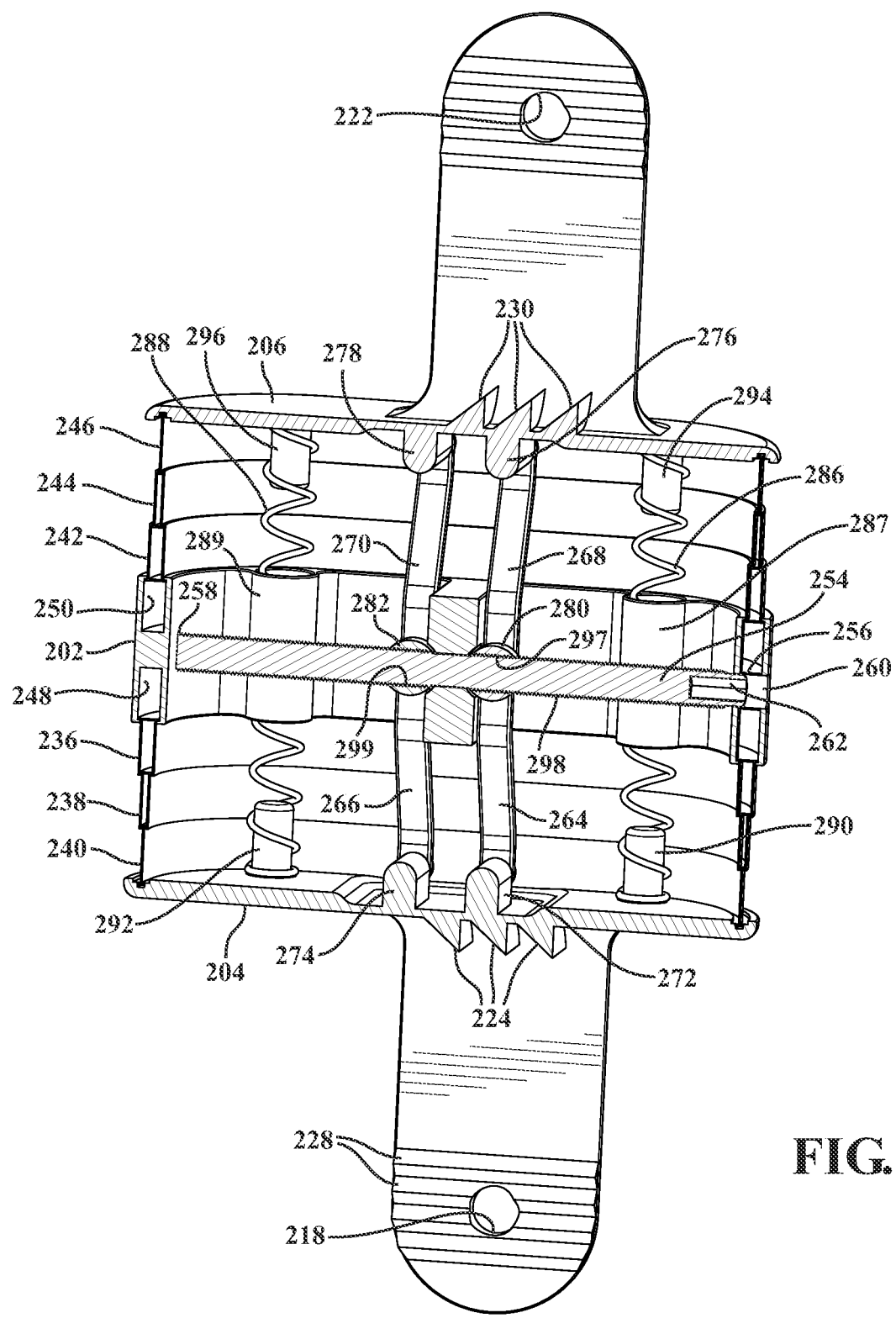
FIG. 11 is a further cutaway view taken along line 11-11 of FIG. 9 and showing the worm screw and axially translating linkages in the expanded position for separating the upper and lower halves.

As shown in each of FIGS. 10-11, a worm screw 254 is provided and extends the interior width of the central body 202 such that the screw 254 is rotatably supported at opposite ends 256/258 of the body. An access channel 260 in the body 202 aligns with a front located of the ends (at 256) and allows insertion of a suitable tool bit (not shown) for engaging the any tool bit recess configuration (see hex profile 262) configured in the forward end of the worm screw 254.

Expansion of the jack halves 202/204 between the configurations of FIGS. 10-11 is facilitated by first and second pairs of linkages, these depicted by lower linkage arms 264/266 and upper linkage arms 268/270. As best shown in FIG. 11, the outer ends of the linkage arms each include a crosswise projecting sleeve or cylinder mount (not shown) which seats within an annular channel configured into a base support location (see lower at 272/274 and upper 276/278) integrated into inside locations of the spinal jack base surfaces 204/206.

As further shown, the inner ends of the linkage arms 264/266 and 268/270 are rotatably supported (via a journaled collar or other bearing support) to first and second worm screw mounted portions 280 and 282, these further being interiorly threaded to inter-engage opposing exterior threads 298 configured on the worm screw 254 and so that, upon rotation of the worm screw via engagement of the tool bit at the forward receiving end 260, the mounted portions 280/282 are caused to displace inwardly towards one another from between the retracted position of FIG. 10 and the expanded position of FIG. 11, at which point the linkages are arranged so that the worm screw portions 280/282 abut opposite sides of a central positioned support 284 through which the worm screw extends.

Pairs of coil springs are provided (one of which is shown at 286/288 in the expanded cutaway of FIG. 11) and which extend through pockets 287 and 289 in the central body 202 and engage around inwardly projecting posts 290/292 and 294/296 integrated into interior locations of the lower 204 and upper 206 spinal jack halves. The outward bias introduced by the springs assists in providing an ongoing bias against the linkage and worm screw to maintain the positioning of the jack halves at the adjusted position. By this construction, precise and secure adjustment of the spinal jack is possible, by virtue of the thread patterns (see again at 298) which are configured upon the exterior of the rotatable worm shaft 254, these rotatably inter-engaging with the previously described opposing interior threads (see at 297 and 299) for the worm screw mounted portions 280/282.

Figure 12:
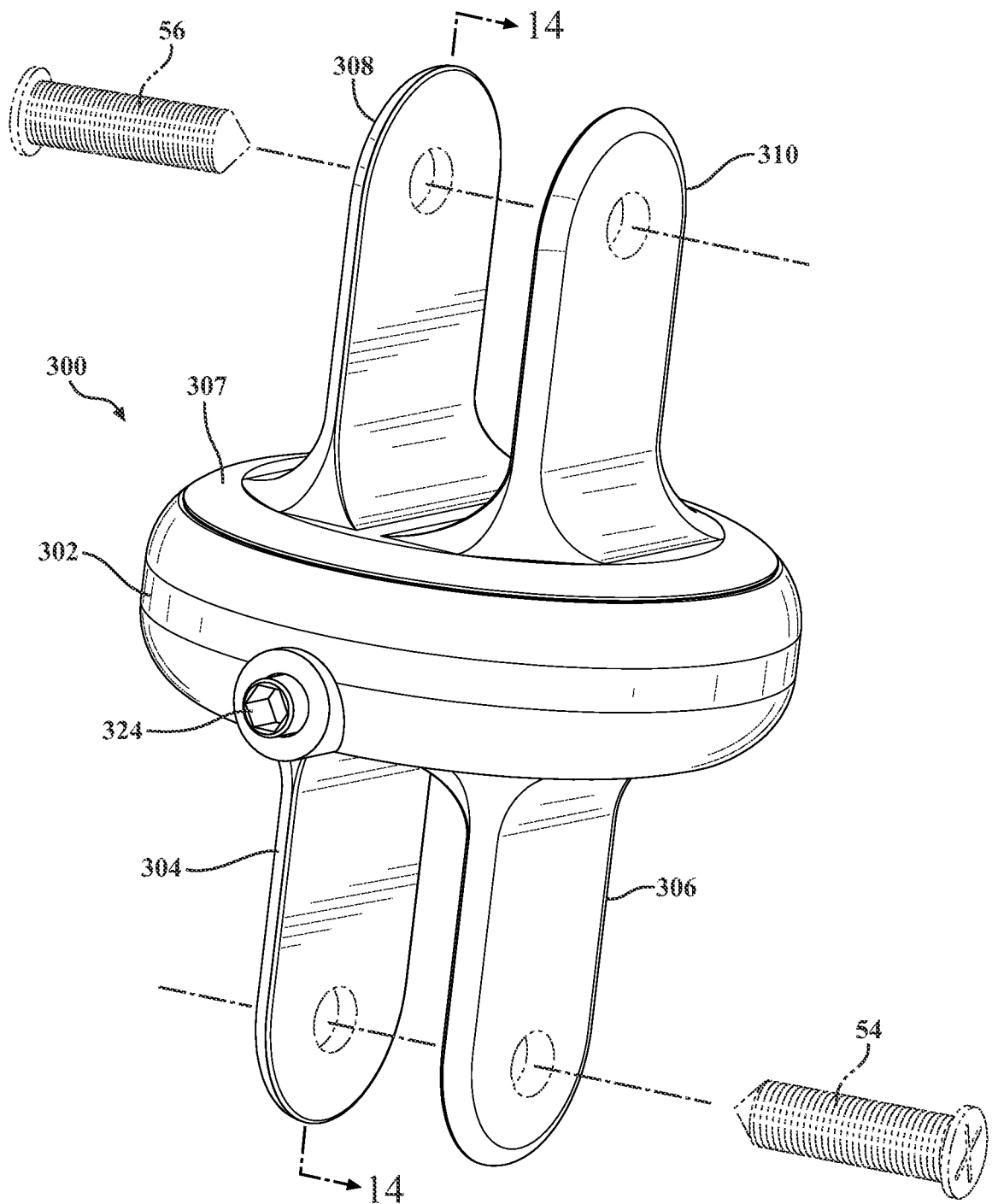
FIG. 12 is a perspective view of a combination worm screw and axial displacement scissor lift spinal jack assembly in a retracted position and according to a further variant.

Proceeding to FIG. 12, a perspective view of a combination worm screw and axial displacement scissor lift spinal jack assembly in a retracted position and according to a further variant 300 which is similar in numerous respects to that shown at 200, with the redesigned jack 300 including a main generally circular or donut shaped body 302 incorporating a pair of spaced apart extending portions 304/306 defining a lower gripping location for securing a first superior articular process. An upper jack body includes a base disk shape 307 from which upwardly extends a further pair of spaced apart portions 308/310 which define a further gripping location for securing a second superior articular process (again at 2 and 4 in FIG. 1), and which as previously described can include any type of textured or ribbed locations for assisting in gripping the superior articular process, as well as aligning apertures for mounting therethrough a suitable metal bolt or screw.

Figure 14:
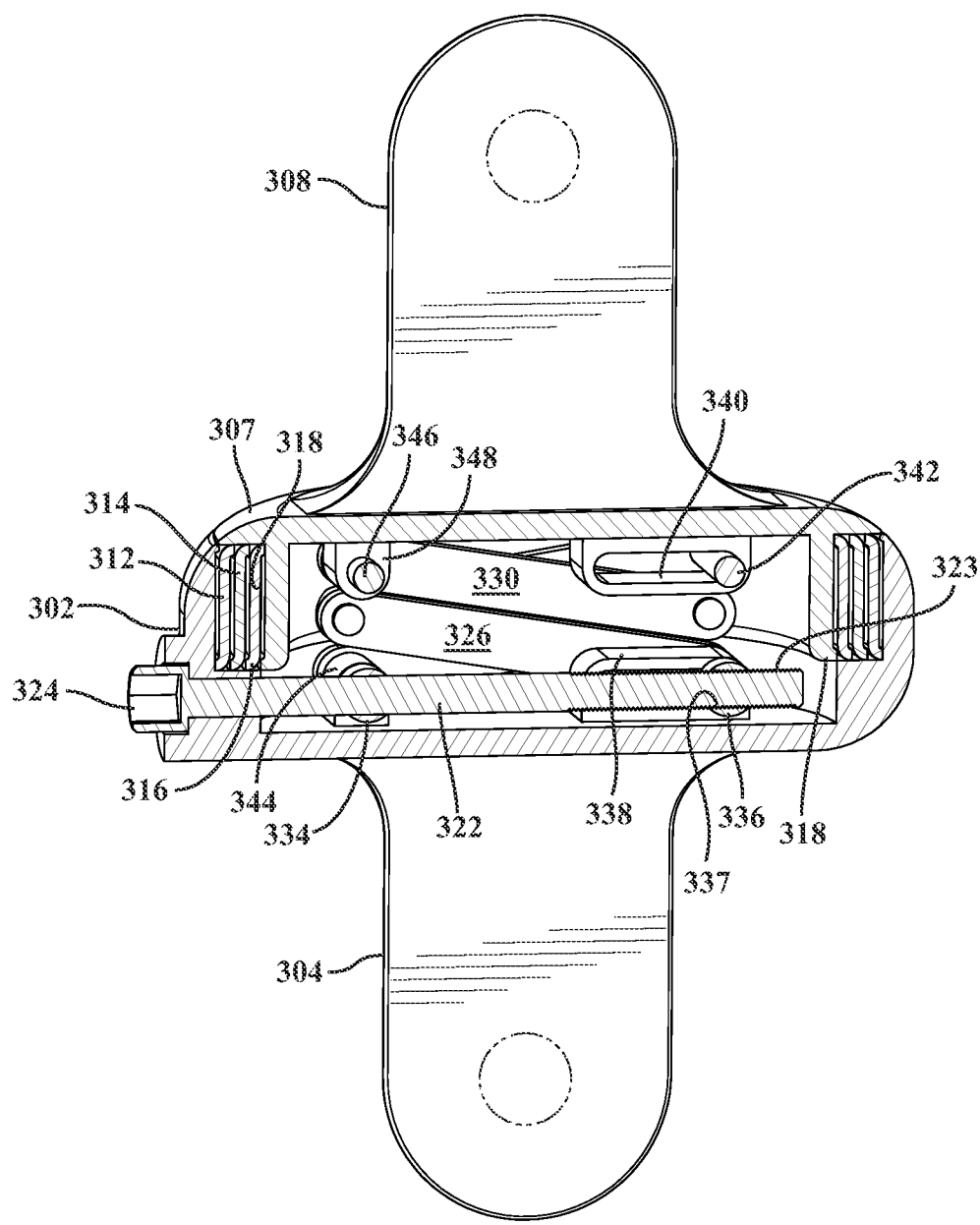
FIG. 14 is a length cutaway view taken along line 14-14 of FIG. 12 and showing the worm screw and axial displacement scissor lifts in the retracted position.
Figure 15:
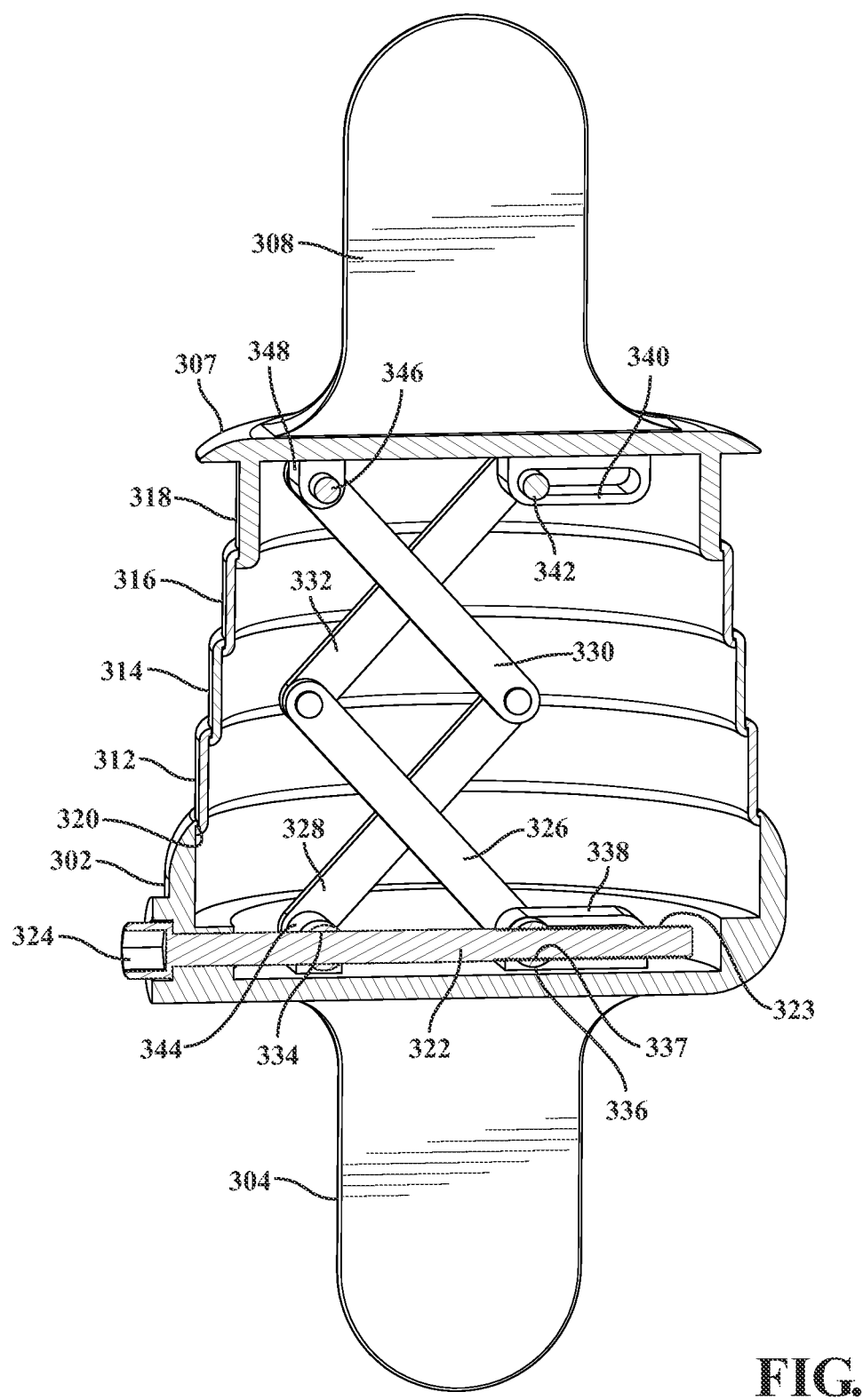
FIG. 15 is a further cutaway taken along line 15-15 of FIG. 13 and showing the worm screw and axial displacement scissors in the expanded position for separating the upper and lower halves.

A similar arrangement of interlocking and inter-expanding annular skirts 312, 314 and 316 are provided which, upon expanding the upper jack half 307 in the manner depicted in FIG. 15, likewise isolates and protects the interior of the scissor linkage employed for adjusting the jack in use. As further again best shown in FIG. 15, the upper body 307 includes an inner annular extending rim 318, about which telescopically seat the annular skirts, with a lowermost and outwardly angled rim edge for gripping the uppermost expandable skirt 316, in turn inter-telescoping successively with the lower skirts 312/314, with a further inside notched edge 320 of the base or lower jack half 302 (see again FIG. 15) securing the lower skirt 312 in order to maintain the integrity of the skirts between their collapsed (FIG. 14) and expanded (FIG. 15) positions.

A similar exteriorly threaded worm screw 322 (see FIGS. 14-15 with exterior threads 323) is provided which is supported across the extending width of the lower jack half body 302 and is rotatably supported at opposite interior locations of the donut shaped body 302. A forward tool (again typically hex bit) receiving location 324 of the worm screw 322 extends through an aperture in the main body 302.

The linkages of the variant 200 are substituted in this embodiment (300) in favor of scissor lifts (see X shaped configured first and second pairs of interconnected pairs of arms 326/328 and 330/332 as best shown in FIG. 15). The first or lower pair of arms 326/328 are connected via interiorly threaded and worm gear supported portions 334 and 336 (see interior threads 335 and 337 which mate with exterior threads 323 of the worm screw 322), with opposite and upper most ends of the second pair of scissor arms 330/332 connecting to underside locations of the upper disk shaped body 307.

The supported ends of the pairs of scissor arms can further include at least one guide or track location for ensuring non-binding operation of the linkage arms during their scissor-like motion, and which is depicted by supporting track 338 associated with the lower scissor link 326 for seating the selected worm gear supported portion 336 and further supporting track 340 associated with the upper scissor link 332 through which an end pin 342 of the link arm 332 is received. The other gear supported portion 334 is depicted affixed to a given location within the lower main jack body 302 (see further base mounting location 344), with an extending pin end 346 of the link arm 330 seating through a further fixed and rotatably supporting location 348 located upon an underside of the upper body 306.

Figure 16:
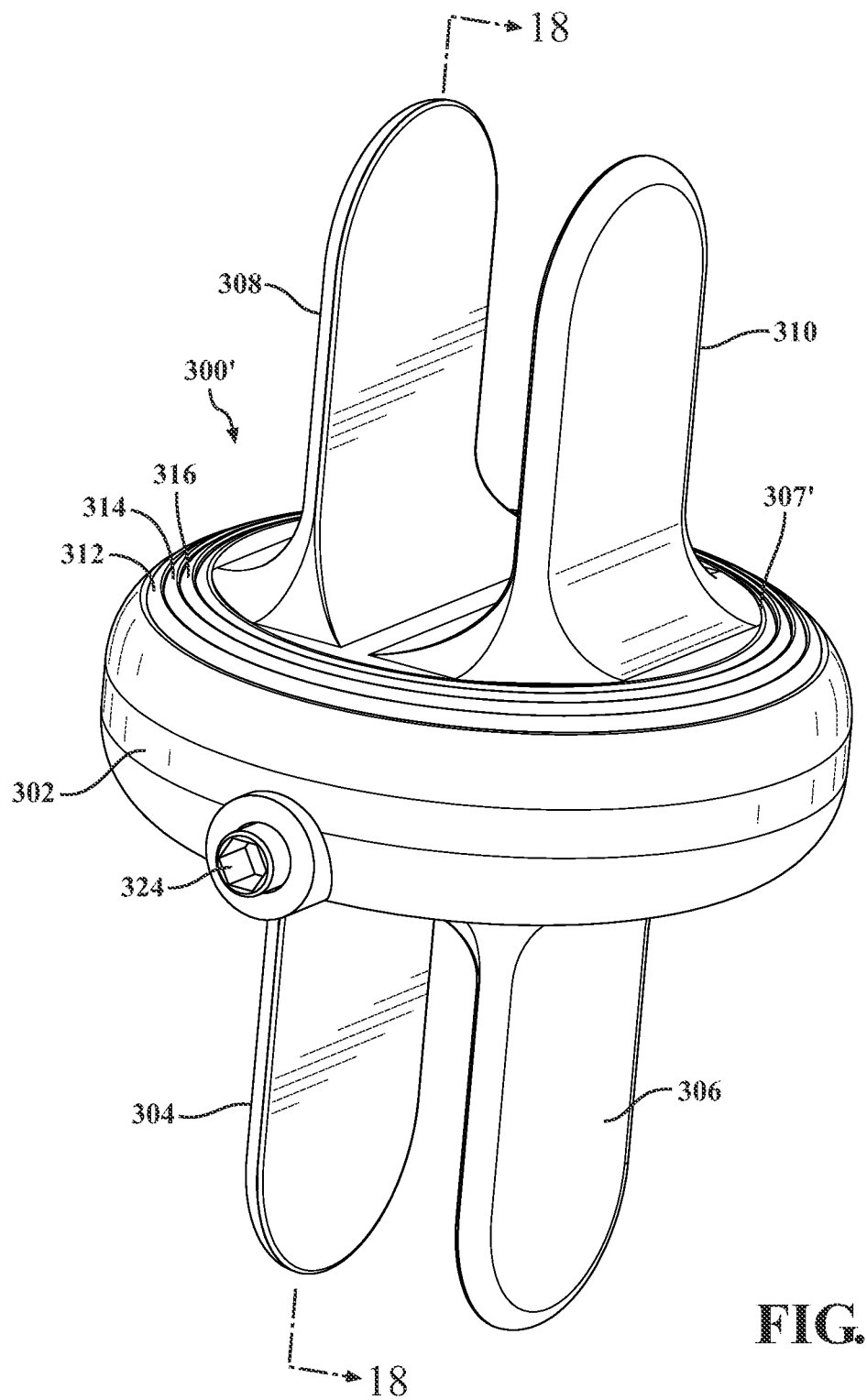
FIG. 16 is a perspective view of a combination worm screw and axial displacement scissor lift spinal jack assembly which is a subset variant of FIG. 12 in a retracted position.

FIG. 16 is a perspective view of a combination worm screw and axial displacement scissor lift spinal jack assembly, at 300', which is a subset of the variant 300 of FIG. 12 in a retracted position. The version 300' of FIGS. 16-19 is substantially identical to that previously described at 300, with the exception that the outer annular skirt portion of the disk shaped body 307 as depicted in FIG. 12 is reduced in profile as shown at 307' so that the upper rim edges of the coaxially arrayed and annular extending skirts 312, 314 and 316 are visible (see as shown in FIG. 16 as compared to FIG. 12).

Figure 13:
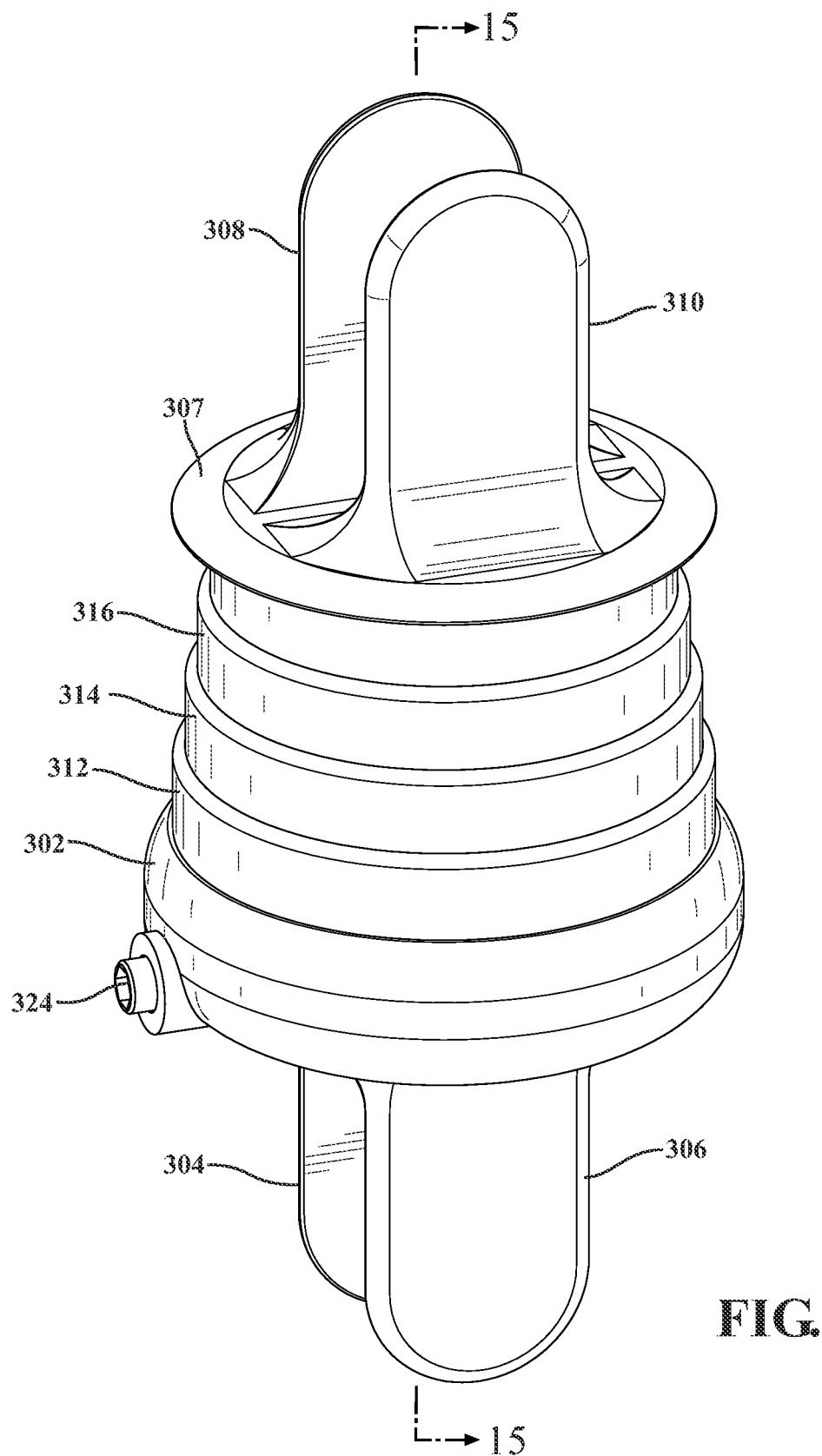
FIG. 13 is a succeeding view to FIG. 12 depicting the spinal jack in an expanded position.
Figure 17:
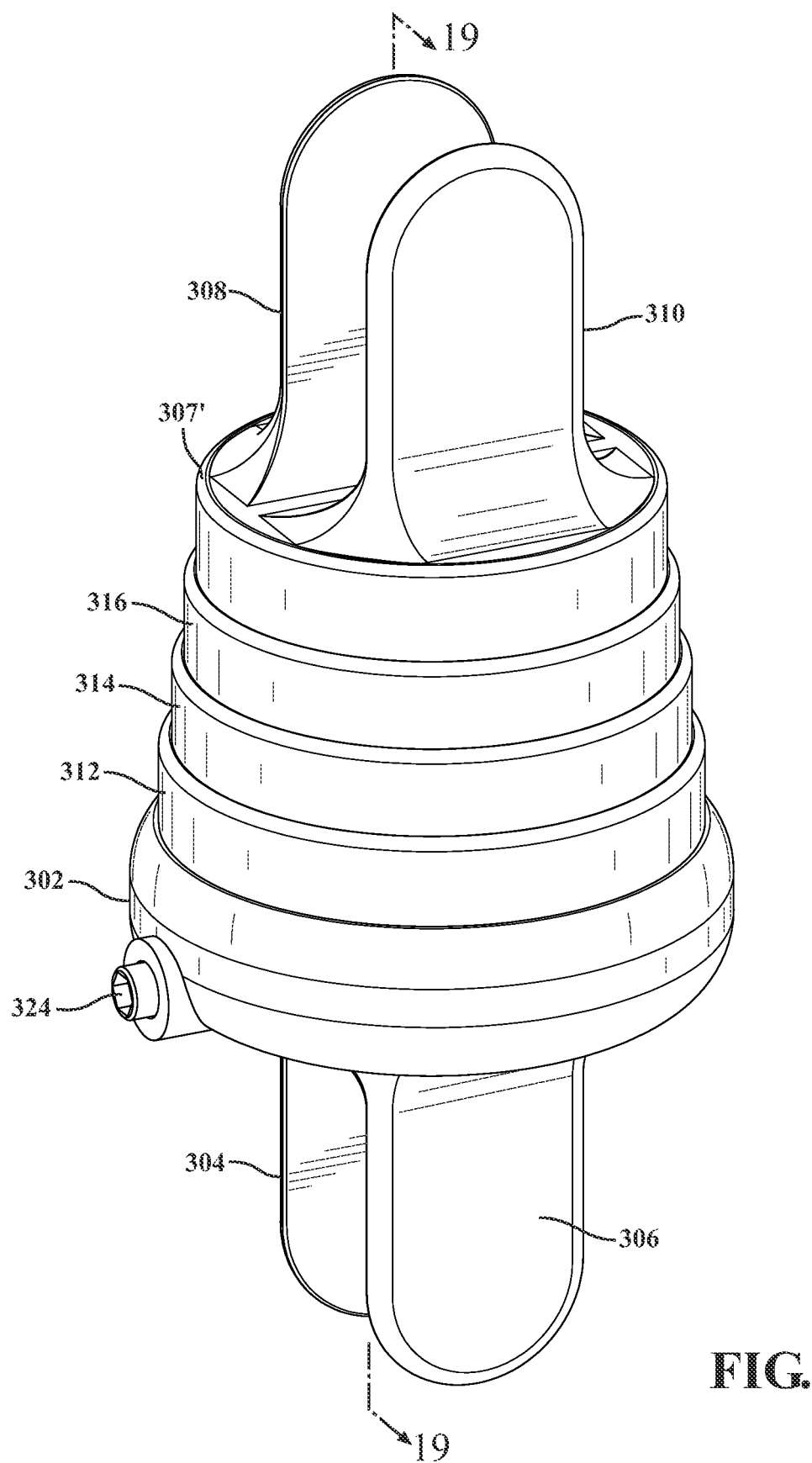
FIG. 17 is a succeeding view to FIG. 16 depicting the spinal jack in an expanded position and better illustrating a redesigned and non-perimeter extending skirt edge associated with the upper separating half of the jack as compared to that shown in the related variant of FIG. 13.

FIG. 17 is a succeeding view to FIG. 16 depicting the spinal jack in an expanded position and better illustrating a redesigned and non-perimeter extending skirt edge, again at 307', associated with the upper separating half of the jack as compared to that shown in the related variant of FIG. 13.

Figure 18:
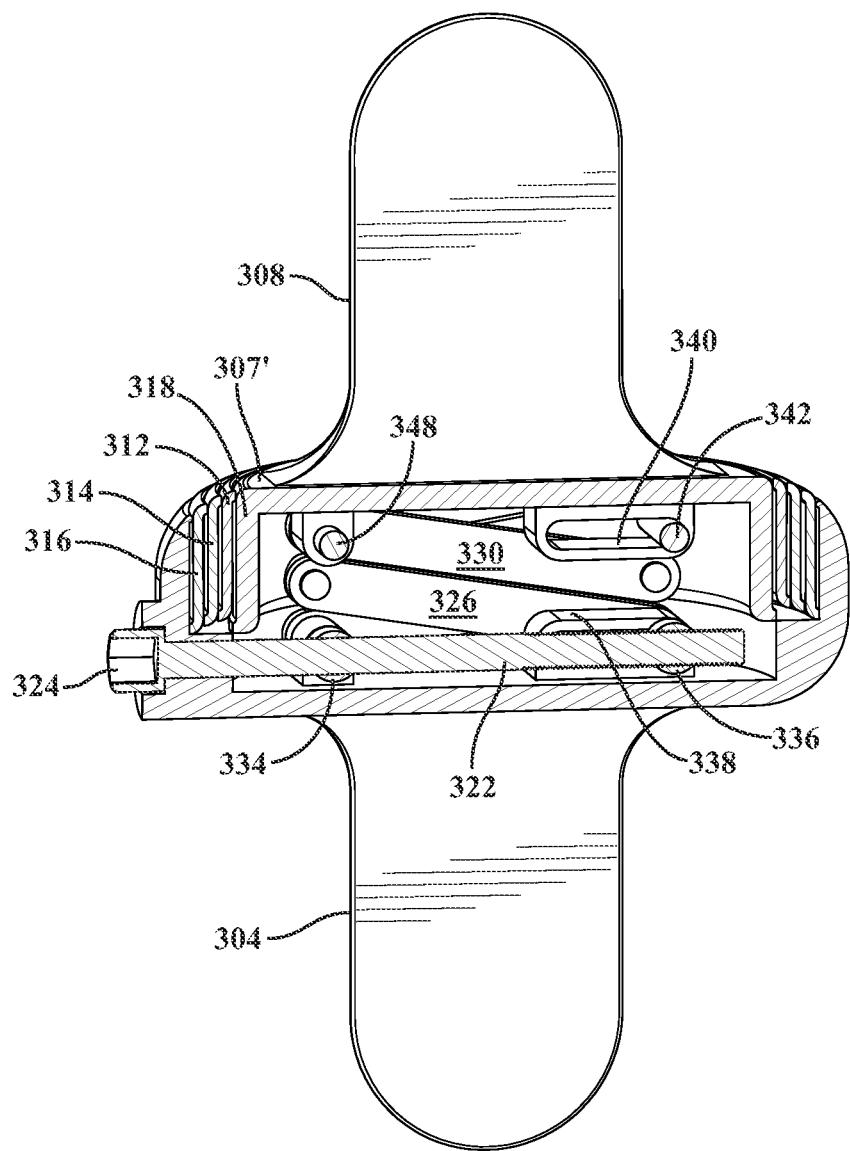
FIG. 18 is a length cutaway view taken along line 18-18 of FIG. 16 and showing the worm screw and axial displacement scissor lifts in the retracted position.
Figure 19:
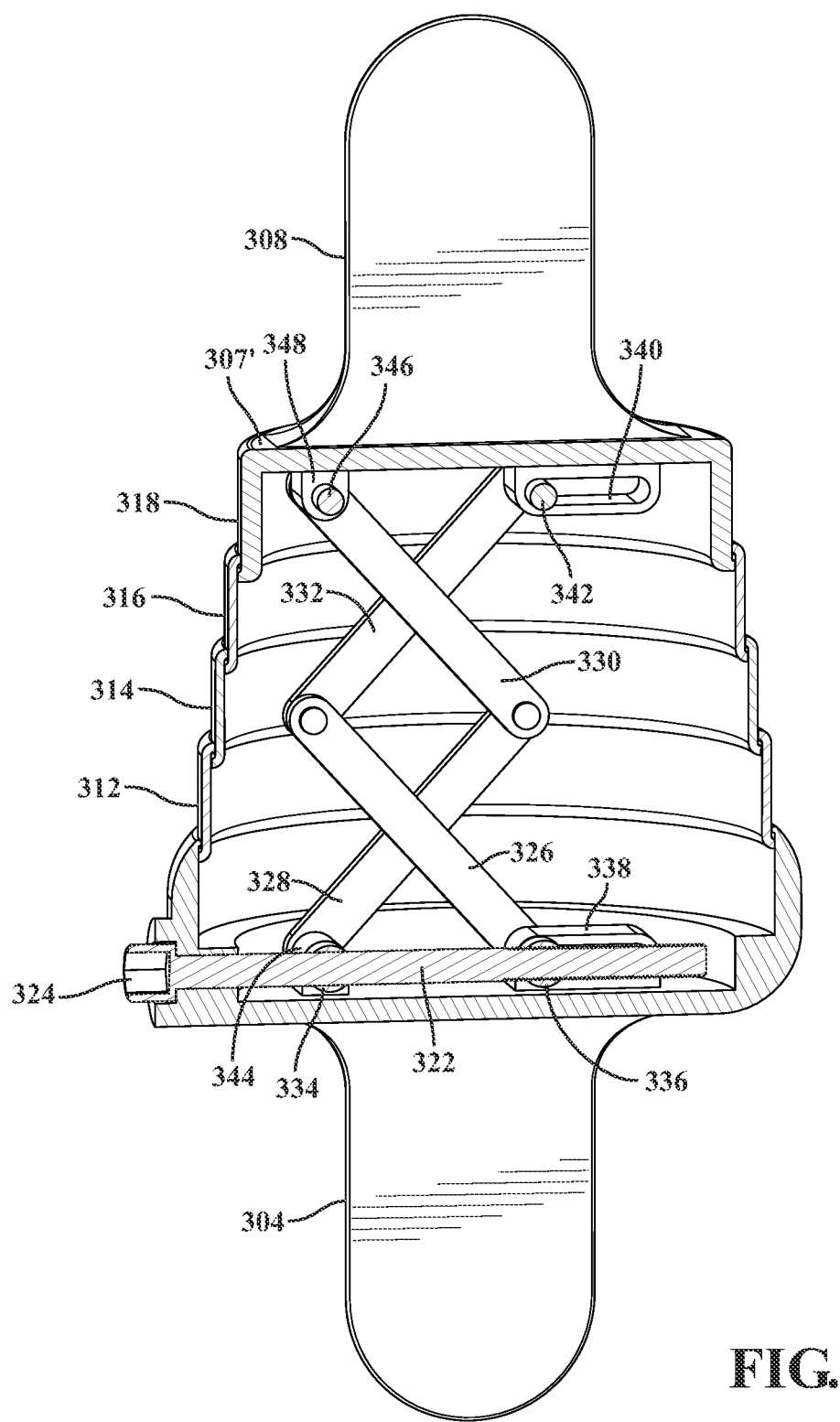
FIG. 19 is a further cutaway taken along line 19-19 of FIG. 17 and showing the worm screw and axial displacement scissors in the expanded position for separating the upper and lower halves.

FIG. 18 is a length cutaway view taken along line 18-18 of FIG. 16 and showing the worm screw and axial displacement scissor lifts in the retracted position, with FIG. 19 a further cutaway taken along line 19-19 of FIG. 17 and showing the worm screw and axial displacement scissors in the expanded position for separating the upper and lower halves.

Having described my invention, other and additional preferred embodiments will become apparent to those skilled in the art to which it pertains, and without deviating from the scope of the appended claims. The detailed description and drawings are further understood to be supportive of the disclosure, the scope of which being defined by the claims. While some of the best modes and other embodiments for carrying out the claimed teachings have been described in detail, various alternative designs and embodiments exist for practicing the disclosure defined in the appended claims.

The foregoing disclosure is further understood as not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, a person of ordinary skill in the art will recognize that changes may be made in form and detail without departing from the scope of the present disclosure. Thus, the present disclosure is limited only by the claims.

In the foregoing specification, the disclosure has been described with reference to specific embodiments. However, as one skilled in the art will appreciate, various embodiments disclosed herein can be modified or otherwise implemented in various other ways without departing from the spirit and scope of the disclosure. Accordingly, this description is to be considered as illustrative and is for the purpose of teaching those skilled in the art the manner of making and using various embodiments of the disclosure. It is to be understood that the forms of disclosure herein shown and described are to be taken as representative embodiments. Equivalent elements, materials, processes or steps may be substituted for those representatively illustrated and described herein. Moreover, certain features of the disclosure may be utilized independently of the use of other features, all as would be apparent to one skilled in the art after having the benefit of this description of the disclosure. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

Additionally, all numerical terms, such as, but not limited to, "first", "second", "third", "primary", "secondary", "main" or any other ordinary and/or numerical terms, should also be taken only as identifiers, to assist the reader's understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application. Additionally, any signal hatches in the drawings/figures should be considered only as exemplary, and not limiting, unless otherwise specifically specified.

The invention claimed is:

1. A spinal jack adapted for installation between first and second vertebral processes, comprising:
   a central body supporting first and second inter-expandable jack halves between retracted and expanded positions;
   each of said jack halves further including gripping portions adapted for engaging the vertebral processes;
   a geared mechanism having a tool bit engageable drive gear and inter-engaging outer driven gears which in turn displace said jack halves relative to said central body for expanding or retracting the jack halves in order to establish a corrected adjusted orientation between the processes; and
   said drive gear having an inner aperture seating an outwardly biased spring loaded pin for preventing rotation thereof and displacement of said jack halves, with engagement of a tool bit resulting in an inward displacement of a forward portion of said pin in order to disengage from a surrounding surface profile of said inner aperture to permit rotation of said drive gear and inter-engaging outer gears.

2. The spinal jack of claim 1, further comprising a spring providing an outward bias against said jack halves.

3. The spinal jack of claim 1, said body and inter-expandable jack halves further comprising any medical grade metal or plastic.

4. The spinal jack of claim 1, said gripping portions further comprising a pair of spaced apart arms defining a pocket adapted to receive the vertebral process therebetweeen.

5. The spinal jack of claim 4, said pockets each further including textured surfaces for providing additional gripping of the vertebral processes.

* * * * *